US006583307B2

(12) United States Patent
Nolan et al.

(10) Patent No.: US 6,583,307 B2
(45) Date of Patent: Jun. 24, 2003

(54) CONVENIENT AND EFFICIENT SUZUKI-MIYAURA CROSS-COUPLING CATALYZED BY A PALLADIUM/DIAZABUTADIENE SYSTEM

(75) Inventors: Steven P. Nolan, New Orleans, LA (US); Gabriela Grasa, New Orleans, LA (US)

(73) Assignee: University of New Orleans Research and Technology Foundation, Inc., New Orleans, LA (US)

(*) Notice: Subject to any disclaimer, the term of this patent is extended or adjusted under 35 U.S.C. 154(b) by 0 days.

(21) Appl. No.: 10/092,753

(22) Filed: Mar. 7, 2002

(65) Prior Publication Data

US 2002/0198423 A1 Dec. 26, 2002

Related U.S. Application Data

(60) Provisional application No. 60/274,125, filed on Mar. 7, 2001.

(51) Int. Cl.[7] ....................... C07C 15/14; C07C 255/50; C07C 25/18; C07C 45/61; C07C 41/24

(52) U.S. Cl. ....................... 558/411; 560/102; 568/315; 568/316; 568/631; 568/642; 570/127; 570/182; 585/469; 585/471

(58) Field of Search ................................ 558/411, 631, 558/642, 315, 316; 560/102; 570/127, 182; 585/469, 471; 502/167, 171

(56) References Cited

U.S. PATENT DOCUMENTS

| | | | | | |
|---|---|---|---|---|---|
| 5,147,840 | A | * | 9/1992 | de Jong et al. ............. | 502/162 |
| 6,194,599 | B1 | * | 2/2001 | Miller et al. ................ | 558/411 |
| 6,235,849 | B1 | * | 5/2001 | Jayaraman et al. ...... | 525/326.7 |
| 6,316,380 | B1 | * | 11/2001 | Nolan et al. ................ | 502/155 |

OTHER PUBLICATIONS

Grasa et al., Convenient and Efficient Suzuki–Miyaura Cross–Coupling Catalyzed by a Palladium/Diazabutadiene System, Organic Letters, Feb. 2001, vol. 3, No. 7, pp. 1077–1080.*

* cited by examiner

*Primary Examiner*—Rosalynd Keys
(74) *Attorney, Agent, or Firm*—Garvey, Smith, Nehrbass & Doody, L.L.C.; Seth M. Nehrbass

(57) ABSTRACT

A $Pd(OAc)_2$/diazabutadiene system has been developed for the catalytic cross-coupling of aryl halides with arylboronic acids. A combination of the diazabutadiene DAB-Cy (1, N,N'-Dicyclohexyl-1,4-dizabutadiene) and $Pd(OAc)_2$ was found to form an excellent catalyst for the Suzuki-Miyaura cross-coupling of various aryl bromides and activated aryl chlorides with arylboronic acids.

4 Claims, 1 Drawing Sheet

CONVENIENT AND EFFICIENT SUZUKI-MIYAURA CROSS-COUPLING CATALYZED BY A PALLADIUM/DIAZABUTADIENE SYSTEM

CROSS-REFERENCE TO RELATED APPLICATIONS

Priority of our U.S. Provisional Patent Application Serial No. 60/274,125, filed Mar. 7, 2001, incorporated herein by reference, is hereby claimed.

STATEMENT REGARDING FEDERALLY SPONSORED RESEARCH OR DEVELOPMENT

This material is based upon work supported by the National Science Foundation under Grant No. 9985213. The Government has certain rights in this invention.

Any opinions, findings, and conclusions or recommendations expressed in this material are those of the inventors and do not necessarily reflect the views of the National Science Foundation.

REFERENCE TO A "MICROFICHE APPENDIX"

Not applicable

BACKGROUND OF THE INVENTION

1. Field of the Invention

The present invention relates to Suzuki-Miyaura cross-coupling reactions. More particularly, the present invention relates to catalysts for Suzuki-Miyaura cross-coupling reactions.

2. General Background of the Invention

The Suzuki-Miyaura cross-coupling reaction, involving the coupling of an arylboronic acid with an organohalide, has proven to be an extremely useful synthetic tool in organic synthesis (1). Although palladium complexes bearing tertiary phosphine ligands are commonly employed (1a) (2), in Suzuki-Miyaura cross-couplings, these catalysts are often sensitive to air oxidation and therefore require air-free handling in order to minimize ligand oxidation. Nucleophilic N-heterocyclic carbenes, the imidazol-2-ylidenes, have recently been used as ancillary ligands for Suzuki-Miyaura cross-coupling reactions with great success (3).

In the specific area of coupling chemistry, catalytic systems which contain supporting ligations other than tertiary phosphine represent a scarcely explored area of investigation. Recently, a Pd(II) cyclometallated imine catalyst able to mediate both Suzuki (4) and Heck (5) reactions has been reported by Milstein. Unfortunately, this system requires high reaction temperatures and leads to products in modest yields.

Incorporated by reference are the paper attached to our U.S. Provisional Patent Application Serial No. 60/274,125 and entitled: "Convenient and Efficient Suzuki-Miyaura Cross-Coupling Catalyzed by a Palladium/Diazabutadiene System" by Gabriela A. Grasa, Anna C. Hillier, and Steven P. Nolan, all references cited therein, and all related papers of which the inventors are authors.

The following U.S. Patent is incorporated herein by reference:

U.S. Pat. No. 6,316,3 80 entitled "Catalyst system comprising transition metal and imidazoline-2-ylidene or imidazolidine-2-ylidene"

BRIEF SUMMARY OF THE INVENTION

The present invention includes a $Pd(OAc)_2$/diazabutadiene system for the catalytic cross-coupling of aryl halides with arylboronic acids and a method of catalytic cross-coupling of aryl halides with arylboronic acids using this system.

DETAILED DESCRIPTION OF THE INVENTION

Based on the Milstein report, we thought a well-known family of ligands, the diazabutadienes, might possibly mediate the Suzuki-Miyaura reaction. The chelating nature of these ligands might also assist in stabilizing catalytic species. Ligands containing the 1,4-diaza-1,3-butadiene skeleton, a-diimines, (DAB-R, Scheme 1—see below) have been known for quite some time (6). The coordination versatility of these ligands, a consequence of the flexibility of the NCCN backbone and the strong s-donor and p-acceptor properties, reflects a very important feature of DAB-R-metal complexes (7). Few investigations have focused on the influence of DAB-R as a supporting ligand in catalytic processes. The most notable exceptions have been the use of metal-diimine complexes to mediate olefin polymerization (8) and alkyne cyclotrimerization (9) processes.

BRIEF DESCRIPTION OF DRAWING

Scheme 1 (see below) shows a Diazabutadiene Ligand.

We now wish to report an additional use of these ligands in the efficient catalytic cross-coupling of aryl halides with arylboronic acids using a combination of Pd(OAc)2/diazabutadiene (DAB-R) as the catalytic system.

Figure 1:
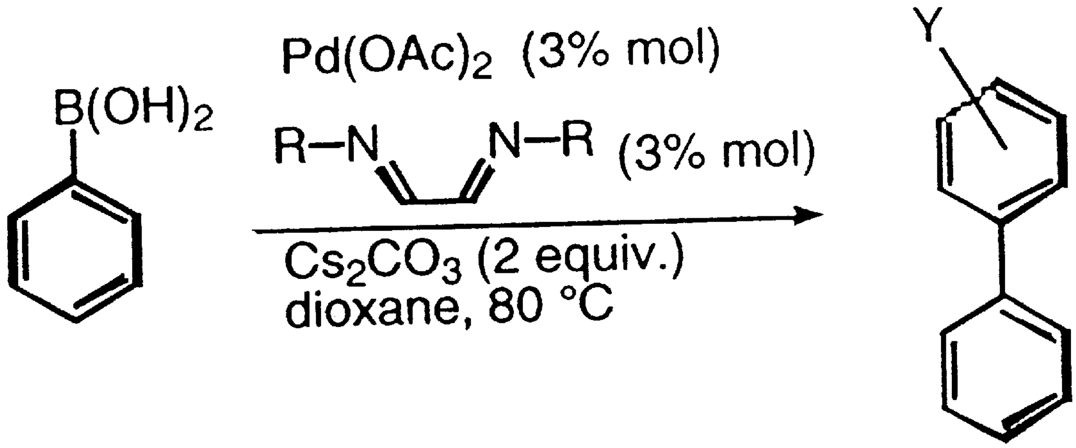

Based on our previous experience in Pd/imidazolium salt catalyzed Suzuki-Miyaura reaction, 3e we observed that the coupling of 4-bromotoluene and phenylboronic acid in the presence of 3 mol % of $Pd(OAc)_2$, 3 mol % DAB-Mes (4) and $Cs_2CO_3$ in dioxane, at 800 C. proceeded to give 4-methylbiphenyl in 85% isolated yield (Table 1, entry 5—see below). Investigation of other diazabutadiene ligands led to the observation that alkyl-diazabutadienes (Table 1, entries 2 and 3) are superior supporting ligands for the Pd-catalyzed Suzuki reaction compared to aryl-diazabutadienes (Table 1, entries 4–8). This reactivity trend is in agreement with the stronger donating ability of alkyl substituents making the ligand more electron rich. Other bis(nitrogen donor) ligands were investigated but considering the electronic argument presented above, it was not surprising to observe a poorer performance of the commercially available ligands 2,2'-bipyridyl (Table 1, entry 9) and 1,10-phenanthroline (Table 1, entry 10).

Table 1 (see below) shows the influence of DAB-R Ligands on the Palladium-Catalyzed Cross-Coupling Reaction of 4-bromotoluene with Phenylboronic Acid. Reaction conditions in Table 1 were: 1.0 mmol of 4-bromotoluene, 1.5 mmol of phenylboronic acid, 2 MMol $Cs_2CO_3$, 3.0 mol % $Pd(OAc)_2$, 3.0 mol % ligand, 3 mL dioxane, 80° C., 3 hr. Isolated yields. All reactions were monitored by GC. Yields are average of two runs.

An investigation of the influence of the base suggested that $Cs_2CO_3$ was the reagent of choice. In turn, $K_2CO_3$, an effective base for the cyclopalladated-imine catalyst for the Suzuki-Miyaura reaction 4 proved to be less effective, leading to a 63% isolated yield (Table 2, entry 9—see below). Other bases such as $Na_2CO_3$, $Ca(OH)_2$, NaOMe, K(OtBu), KOMe and $Ba(OH)_2$ proved to be ineffective for the cross-coupling of 4-bromotoluene with phenylboronic acid (Table 2, entries 2–5,7,8). Moreover, KF, a very effective additive for $Pd(dba)_2$/(tBu)3P-catalyzed Suzuki-Miyaura reaction (10), also proved to be less effective in the present system.

Table 2 (see below) shows the effect of the Base on $Pd(OAc)_2$/DAB-Cy (1)—Catalyzed Cross-Coupling of 4-bromotoluene with Phenylboronic Acid. Reaction conditions in Table 2 were: 1.0 mmol of aryl bromide, 1.5 mmol of phenylboronic acid, 2 mmol base, 3.0 mol % $Pd(OAc)_2$, 3.0 mol % DAB-Cy, 3 mL dioxane, 80° C. Isolated yields. Entries 5,6, & 7 are GC yields. All reactions were monitored by GC. Yields are average of two runs.

As illustrated in Table 3, the palladium-catalyzed Suzuki-Miyaura reaction with the DAB-Cy (1) ancillary ligand proved exceptionally active. Not surprisingly the non-activated aryl bromides (Table 3, entry 3—see below) were easily converted. This reaction could be performed in the air as well, but requires longer reaction times (Table 3, entry 2). Moreover, ortho-substituted substrates also led to excellent yields (Table 3, entries 6 and 7). The catalytic effect was confirmed by running the standard reaction on 4-bromoacetophenone without ligand. The reaction proceeds but it requires much longer reaction times compared to the $Pd(OAc)_2$/DAB-R system (Table 3, entries 4 and 5). Activated aryl chlorides led to moderate to high yields when this catalytic system was employed (Table 3, entries 11 and 12). Attempts to couple the electron-neutral 4-chlorotoluene and the electron-rich 4-chloroanisole were not successful. Investigations regarding the steric and electronic properties of diazabutadiene ligands able to activate the aryl chlorides are presently underway.

Table 3 (see below) shows $Pd(OAc)_2$/DAB-Cy (1)—Catalyzed Cross-Coupling of Aryl Halides with Phenylboronic Acid. Reaction conditions in Table 3 were: 1.0 mmol of aryl halide, 1.5 mmol of phenylboronic acid, 2 mmol $Cs_2CO_3$, 3.0 mol % $Pd(OAc)_2$, 3.0 mol % DAB-Cy, 3 mL dioxane, 80° C. Isolated yields. In entry 2, the reaction was performed in the air. In entry 5, the reaction was performed using $Pd(OAc)_2$ only. In entries 10, 11, 12 & 13 the reaction was performed at 100° C. Entries 10 & 13 are GC yields. All reactions were monitored by GC. Yields are average of two runs.

The effect of varying the aryl boronic acids in the Suzuki-Miyaura cross-coupling reactions was also investigated using 4-bromotoluene as the substrate (Table 4—see below). Para-substituted aryl boronic acids led to excellent yields of the desired products (Table 4, entries 3 and 4), while the sterically hindered 2-methylphenylboronic acid required longer reaction time before affording very good yields of the product (Table 4, entry 2). Attempts to couple 4-bromotoluene with meta-substituted aryl boronic acids like 3-cyanophenylboronic acid or 3-methoxyphenylboronic acid resulted in low yields. The lower reaction rate may be explained in terms of the different electronic properties of meta-substituted boronic acids (11).

Table 4 (see below) shows $Pd(OAc)_2$/DAB-Cy (1)—Catalyzed Cross-Coupling of 4-bromotoluene with Various Arylboronic Acids. Reaction conditions in Table 4 were: 1.0 mmol of 4-bromotoluene, 1.5 mmol of arylboronic acid, 2 mmol $Cs_2CO_3$, 3.0 mol % $Pd(OAc)_2$, 3.0 mol % DAB-Cy, 3 mL dioxane, 80° C. Isolated yields. All reactions were monitored by GC. Yields are average of two runs.

In summary, an unprecedented, general and efficient methodology based on the $Pd(OAc)_2$/DAB-R system has been developed. The use of DAB-R as supporting ligands for the Suzuki-Miyaura cross-coupling reaction represents an interesting alternative to existing catalytic systems based on the use of tertiary phosphine ligands. The $Pd(OAc)_2$/DAB-R system is very efficient in the Suzuki-Miyaura cross-coupling reaction of aryl bromides with aryl boronic acids in terms of reactivity, reaction temperature, reaction time and air-stability. This system represents unprecedented reactivity for a bis(nitrogen) ligand system with regard to reactivity with unactivated and sterically encumbered substrates, as well as activated aryl chlorides. Investigations regarding the utility of $Pd(OAc)_2$/DAB-R systems towards the activation of electron-rich and electron-neutral aryl chlorides, as well as the influence of the steric and electronic factors of DAB-R ligands are ongoing.

Acknowledgment. The National Science Foundation, the Albermarle Corporation and the Petroleum Research Fund administered by the ACS are gratefully acknowledged for support of this research.

Supporting Information Available. Experimental procedure and references to known compounds. This material is free of charge via the Internet at http://pubs.acs.org.

All measurements disclosed herein are at standard temperature and pressure, at sea level on Earth, unless indicated otherwise. All materials used or intended to be used in a human being are biocompatible, unless indicated otherwise.

(1) (a) For a review see: Miyaura, N.; Suzuki, A. *Chem. Rev.* 1995, 95, 2457–2483. (b) Suzuki, A. in *Metal-Catalyzed Cross-Couplings Reactions;* Diederich, F, Stang, P. J., Eds.; Wiley-V C H: Weinheim, 1998; pp 49–97 and references therein. (c) Hamann, B. C.; Hartwig, J. F. *J. Am. Chem. Soc.* 1998, 120, 7369–7370. (d) Reetz, M. T.; Loluner, G.; Schwickardi, R. *Angew. Chem., Int Ed. Engl.* 1998, 37, 481–483. (e) Littke, A. F.; Fu, G. C. *J. Org. Chem.* 1999, 64, 10–11.

(2) Applications of phosphine ligands in homogeneous catalysis: (a) Parshall, G. W.; Ittel, S. *Homogenous Catalysis;* J. Willey and Sons: New York, 1992. (b) Pignolet, L. H., Ed. *Homogenous Catalysis with Metal Phosphine Complexes;* Plenum: New York, 1983.

(3) (a) Regitz, M. *Angew. Chem. Int. Ed. Engl.* 1996, 35, 725–728. (b) Arduengo, A. J. III; Krafczyc, R. *Chem. Zeit.* 1998, 32, 6–14. (c) Herrmann, W. A.; Kocher, C. *Angew. Chem. Int. Ed. Engl.* 1997,36,2163–2187. (d) Herrmann, W. A.; Reisinger, C. P.; Spiegler, M. J. *Organomet. Chem.* 1998,557, 93–96. (e) Zhang, C.; Huang, J.; Trudell, M. T.; Nolan, S. P. *J. Org. Chem.* 1999, 64, 3804–3805. (f) B öhm, V. P. W.; Gstömayr, C. W. K.; Weskamp. T.; Herrmann, W. A. *J. Orgamomet. Chem.,* 2000, 595, 186–190.

(4) Weissman, H.; Milstein, D. *Chem. Commun.* 1999, 1901–1902.

(5) Ohff, M.; Ohff, A.; Milstein, D. *Chem. Commun.* 1999, 357–358.

(6) van Koten, G.; Vrieze, K. *Adv. Organomet. Chem.* 1982, 21, 151–239 and references cited.

(7) (a) Mathur, P.; Ghosh, S.; Sarkar, A.; Rheingold, A. L.; Guzei, I. A. *J. Organomet. Chem.* 1998, 566, 159–164. (b)Lehmann, J. F.; Urquhart, S. G.; Ennis, L. E.; Hitchcock, A. P.; Hatano, K.; Gupta, S.;Denk, M. K. *Organometallics,* 1999,18,1862–1872. (c) Greulich, S.; Kaim, W.; Stange, A.; Stoll, H.; Fiedler, J.; Zalis, S. *Inorg. Chem.* 1996, 35, 3998–4002. (d) Breuer, J.; Fruhauf, H. W.; Smeets, W. J. J.; Spek, A. L. *Inorg. Chim. Acta.* 1999, 291, 438–447.

(8) (a) Johnson, L. K.; Killian, C. M.; Brookhart, M. S. *J. Am. Chem. Soc.* 1995, 117, 6414–6416. (b) Killian, C. M.; Tempel, D. J.; Johnson, L. K.; Brookhart, M. S. *J. Am. Chem. Soc.* 1996, 118, 11664–11665.

(9) van der Poel, H.; van Koten, G.; Kokkes, M.; Stam, C. H. *Inorg. Chem.* 1981, 20,2941–2950.

(10) Littke, A. F.; Dai, C.; Fu, G. C. *J. Am. Chem. Soc.* 2000, 122, 4020–4028.

(11) March, J. *Advanced Organic Chemistry;* J. Wiley and Sons: New York, 1992, pp. 278–286.

TABLE 1
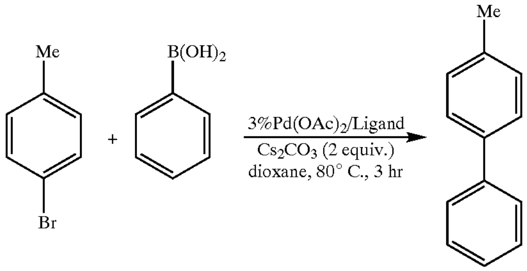
| entry | ligand | yield |
|---|---|---|
| 1 | No L | 30 |
| 2 | 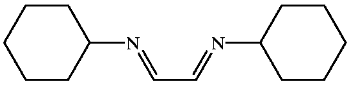 (1) | 99 |
| 3 | 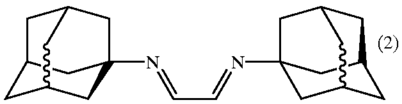 (2) | 93 |
| 4 | 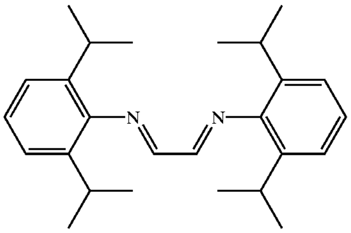 (3) | 80 |
| 5 | 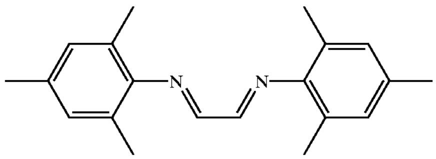 (4) | 85 |
| 6 | 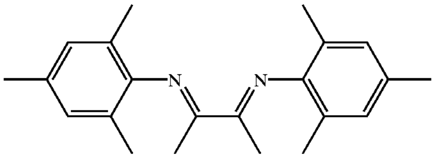 (5) | 78 |
| 7 | 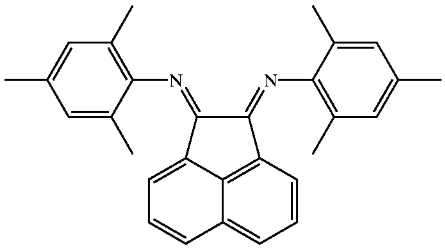 (6) | 79 |
| 8 | 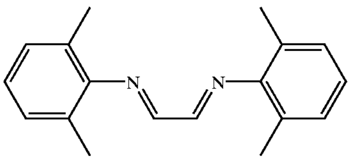 (7) | 60 |
TABLE 1-continued
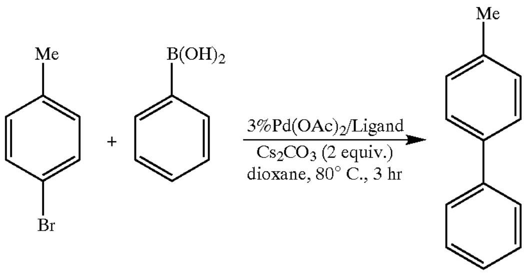
| entry | ligand | yield |
|---|---|---|
| 9 | 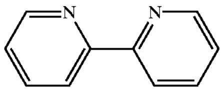 | 13 |
| 10 | 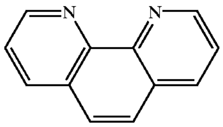 | NR |
SCHEME 1
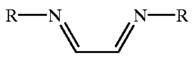
R = aryl and alkyl
TABLE 2
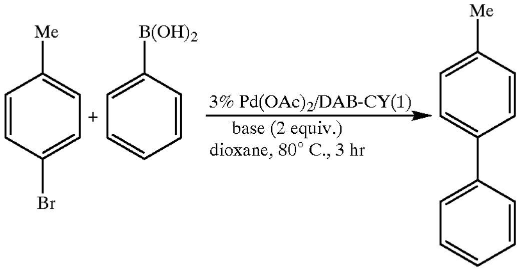
| entry | base | yield |
|---|---|---|
| 1 | None | NR |
| 2 | $Na_2CO_3$ | NR |
| 3 | $Ca(OH)_2$ | NR |
| 4 | NaOMe | NR |
| 5 | K(O$^t$Bu) | 10 |
| 6 | TBAF | 11 |
| 7 | KOMe | 14 |
| 8 | $Ba(OH)_2$ | 44 |
| 9 | $K_2CO_3$ | 63 |
| 10 | KF | 78 |
| 11 | CsF | 87 |
| 12 | $Cs_2CO_3$ | 99 |

TABLE 3
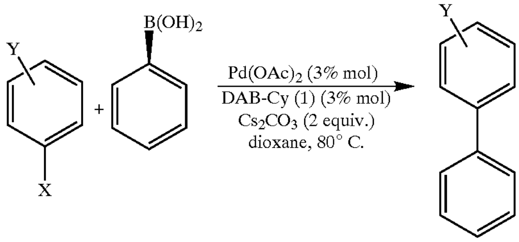
| entry | aryl halide | product | time (h) | yield (%) |
|---|---|---|---|---|
| 1 | 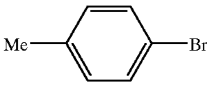 | 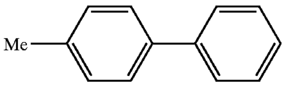 | 3 | 99 |
| 2 | 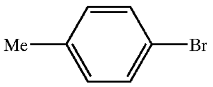 | 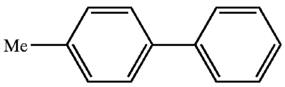 | 5 | 90 |
| 3 | 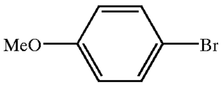 | 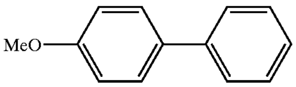 | 5 | 95 |
| 4 | 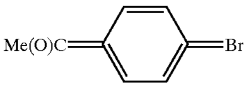 | 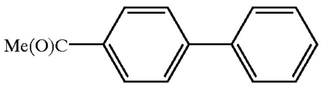 | 1 | 98 |
| 5 | 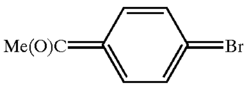 | 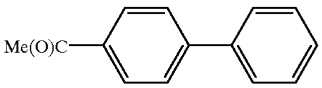 | 20 | 99 |
| 6 | 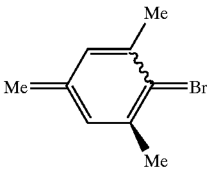 | 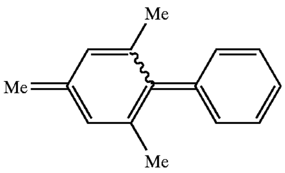 | 4 | 97 |
| 7 | 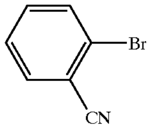 | 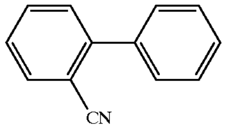 | 1 | 98 |
| 8 | 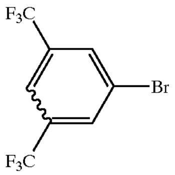 | 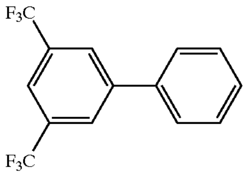 | 2 | 95 |
| 9 | 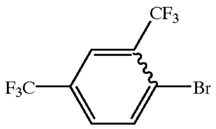 | 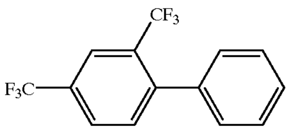 | 21 | 98 |
| 10 | 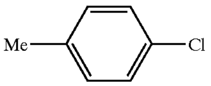 | 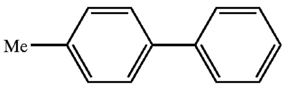 | 4.5 | 20 |

TABLE 3-continued
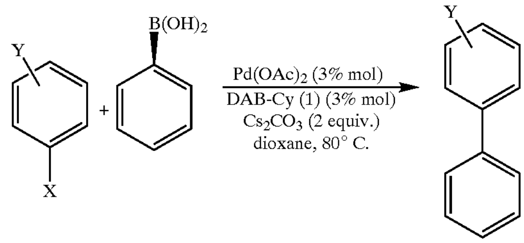
| entry | aryl halide | product | time (h) | yield (%) |
|---|---|---|---|---|
| 11 | 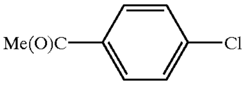 | 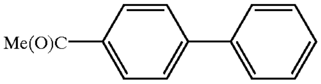 | 4 | 98 |
| 12 | 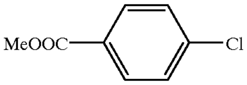 | 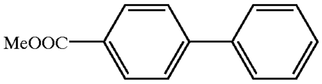 | 5 | 85 |
| 13 | 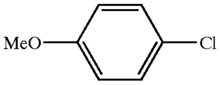 | 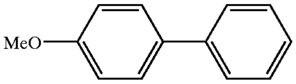 | 24 | 35 |
TABLE 4
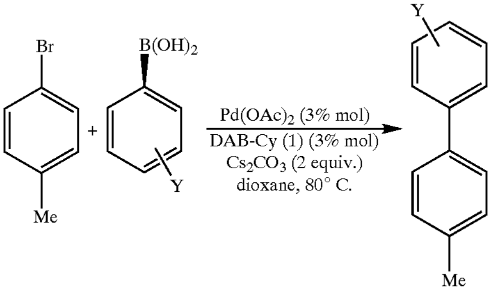
| entry | aryl boronic acid | product | time (h) | yield (%) |
|---|---|---|---|---|
| 1 | 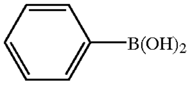 | 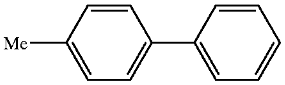 | 3 | 99 |
| 2 | 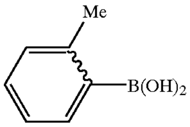 | 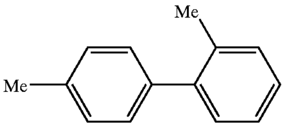 | 10 | 86 |
| 3 | 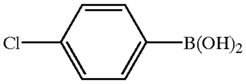 | 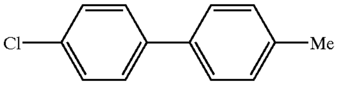 | 6 | 99 |
| 4 | 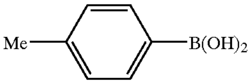 | 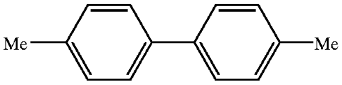 | 2.5 | 96 |
| 5 | 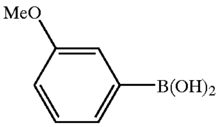 | 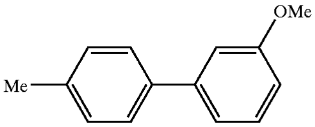 | 24 | 67 |

TABLE 4-continued

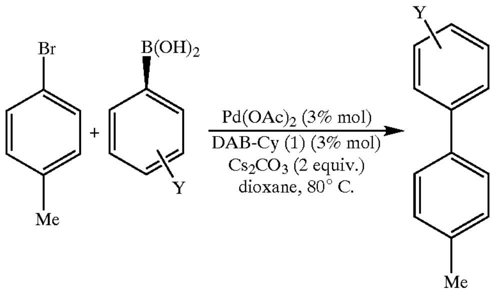

| entry | aryl boronic acid | product | time (h) | yield (%) |
|---|---|---|---|---|
| 6 | 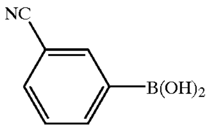 | 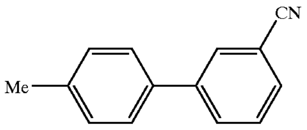 | 24 | 57 |

The forgoing embodiments are presented by way of example only; the scope of the present invention is to be limited only by the following claims.

What is claimed is:

1. A method of catalytic cross-coupling of aryl halides with arylboronic acids using a combination of Pd(OAc)$_2$ and diazabutadiene as the catalytic system.

2. The method of claim 1, wherein the aryl halides are from the group consisting of aryl bromides and activated aryl chlorides.

3. The method of claim 1, wherein the diazabutadiene is DAB-Cy (1, N,N'-Dicyclohexyl-1,4-diazabutadiene).

4. The method of claim 2, wherein the diazabutadiene is DAB-Cy (1, N,N'-Dicyclohexyl-1,4-diazabutadiene).

* * * * *